United States Patent [19]

Tabushi et al.

[11] 4,174,428
[45] Nov. 13, 1979

[54] HEAVY METAL ION ADSORBENTS

[75] Inventors: Iwao Tabushi, No. 15-27, 3-chome, Maidashi, Higashi-ku, Fukuoka-shi, Fukuoka-ken, Japan; Hidefumi Kato, Kurume, Japan; Yoichi Taniguchi, Ogori, Japan; Yasuhisa Kuroda, Osaka, Japan

[73] Assignee: Iwao Tabushi, Kyoto, Japan

[21] Appl. No.: 873,513

[22] Filed: Jan. 30, 1978

[30] Foreign Application Priority Data

Mar. 9, 1977 [JP] Japan .................................. 52/24884
Mar. 9, 1977 [JP] Japan .................................. 52/24885
Mar. 9, 1977 [JP] Japan .................................. 52/24886

[51] Int. Cl.² ........................ C08F 8/00; C07D 257/02
[52] U.S. Cl. ............................ 525/334; 260/239 BC; 423/24; 423/139; 526/261; 521/32; 525/328; 525/375
[58] Field of Search ................ 260/239 BC; 521/32; 526/50, 21, 261

[56] References Cited

U.S. PATENT DOCUMENTS

| B 403,326 | 1/1976 | Richman .................. 260/239 BC |
| 2,840,545 | 6/1958 | Yost ............................ 521/32 |
| 3,118,831 | 1/1964 | Morris ........................ 521/32 |
| 3,423,336 | 1/1969 | Bufton et al. ............... 521/32 |
| 3,828,023 | 8/1974 | Cornier et al. ............. 260/239 BC |
| 3,860,576 | 1/1975 | Ham et al. ................. 260/239 BC |

FOREIGN PATENT DOCUMENTS 451719 5/1973 U.S.S.R. .................................. 526/60

Primary Examiner—Alton D. Rollins
Assistant Examiner—D. B. Springer
Attorney, Agent, or Firm—Frishauf, Holtz, Goodman & Woodward

[57] ABSTRACT

A heavy metal ion adsorbent represented by the following general formula:

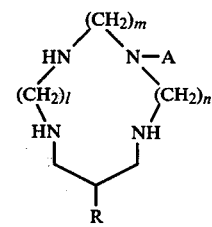

wherein l, m, and n are 2 or 3, respectively; R is an alkyl group containing 4 to 6 carbon atoms which is substituted by an amino group in the ω-position; and A is hydrogen or a synthetic resin.

14 Claims, No Drawings

HEAVY METAL ION ADSORBENTS

BACKGROUND OF THE INVENTION

1. Field of the Invention

This invention relates to adsorbents for heavy metal ions. More particularly, it is concerned with novel adsorbents for heavy metal ions, which are cyclic tetramines containing specific substituents and synthetic resins with the cyclic tetramines bonded thereto.

2. Description of the Prior Art

Heavy metal ion adsorbents hitherto used to remove heavy metal ions contained in waste water, such as copper, nickel, mercury and the like ions include activated carbon, kieselguhr, ion exchange resins, chelate resins and the like. These adsorbents, however, have disadvantages; activated carbon, kieselguhr and ion exchange resins are inferior in selective adsorption ability for heavy metal ions, and chelate resins are inferior in selectivity, particularly among heavy metal ions.

Thus, heavy metal ion adsorbents have long been desired which do not have the disadvantages of the conventional adsorbents.

SUMMARY OF THE INVENTION

The principal object of this invention is to provide heavy metal ion adsorbents having excellent adsorption characteristics: excellent selective adsorption ability for heavy metal ions generally and also between heavy metal ions.

It has now been discovered that cyclic tetramines substituted by a specific substituent at a ring carbon atom and synthetic resins to which the cyclic tetramines are bonded, have excellent adsorption characteristics.

Thus, this invention provides heavy metal ion adsorbents represented by the following general formula:

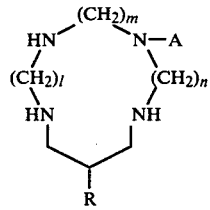

wherein l, m and n are 2 or 3, respectively; R is an alkyl group containing 4 to 6 carbon atoms which is substituted by an amino group in the ω-position; and A is hydrogen or a synthetic resin.

DETAILED DESCRIPTION OF THE INVENTION

In Formula (I), R is, as described above, $C_4$–$C_6$ alkyl group containing an amino group in the ω-position. Typical examples are —$CH_2CH_2CH_2CH_2NH_2$, —$CH_2CH_2CH_2CH_2CH_2NH_2$, etc. In addition, those alkyl groups containing side chains can be used.

Representative compounds represented by the general formula (I) are given below:

Compounds represented by the formula (II):

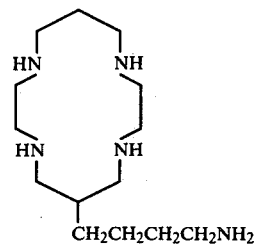

Compounds represented by the formula (III):

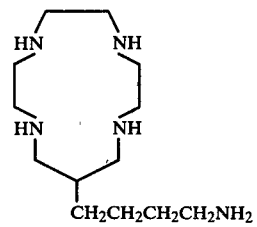

Compounds represented by the formula (IV):

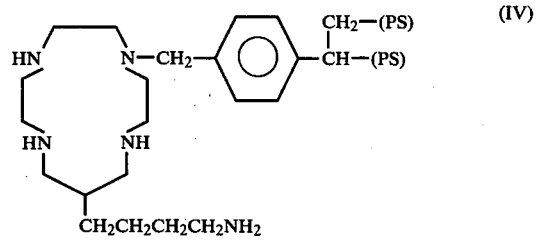

wherein (PS) is polystyrene.

Compounds represented by the formula (V):

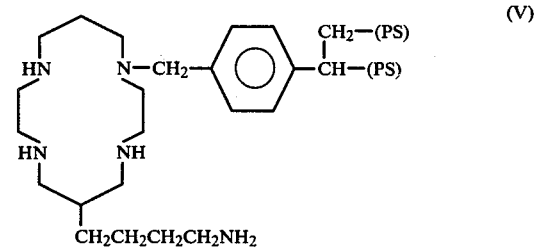

wherein (PS) is polystyrene.

Heavy metal ion adsorbents represented by the general formula (I) in which A is hydrogen; i.e., cyclic tetramines with a specific substituent introduced therein can be synthesized by various procedures. In general, they are synthesized by reacting chain-like tetramines and ω-cyanoalkyl malonates, and reducing the resulting cyclic products.

Preferred chain-like tetramines are, for example, triethylenetetramine, 1,4,8,11-tetraazaundecane, 1,5,9,13-tetraazatridecane and the like. Of these compounds, 1,4,8,11-tetraazaundecane, for example, can be obtained by reacting ethylenediamine and 1,3-dibromopropane in the presence of potassium hydroxide in ethanol.

Preferred ω-cyanoalkyl malonates are, for example, diethyl ω-cyanobutyl malonate, which can be formed by reacting diethyl malonate and 4-bromobutane nitrile, and the like.

Cyclization reaction of the above tetramines and ω-cyanoalkyl malonate is effected by stirring them in a polar solvent capable of dissolving them, such as methanol, ethanol, dimethyl formamide or dimethyl sulfoxide while heating under atmospheric pressure over a period of from 3 to 5 days.

This cyclization reaction yields cyclic diamides represented by the general formula (VI):

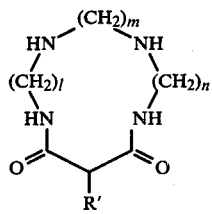

(VI)

wherein l, m and n are 2 or 3, respectively; R' is an alkyl group containing 3 to 5 carbon atoms which contains a cyano group in the ω-position. The thus obtained cyclic compounds are recrystalized from ethanol or the like, isolated and then reduced. This reduction processing can be carried out by, for example, the procedures using reducing agents such as lithium aluminum hydride, diborane, etc., the catalytic reduction process and the like process.

This reduction converts the acid amido (—NHCO) of the ring into —NHCH$_2$, and the cyano group (—CN) of the substituent into —CH$_2$NH$_2$. This results in the formation of the compounds represented by Formula (I), which are the heavy metal ion adsorbents of this invention.

Compounds represented by Formula (VI) which are formed by the above cyclization reaction are given below:

Compounds represented by the formula (VII):

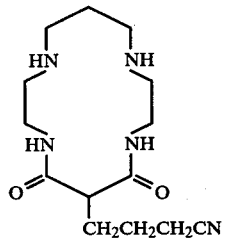

(VII)

Compounds represented by the formula (VIII):

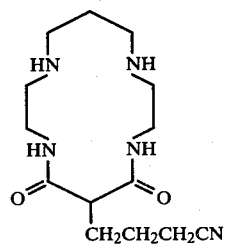

(VIII)

Reduction of the compounds represented by Formula (VII) yields the compounds represented by Formula (II), and reduction of the compounds represented by Formula (VIII) yields the compounds represented by Formula (III).

In producing the heavy metal ion adsorbents represented by Formula (I) in which A is a synthetic resin, chain-like tetramines and ω-cyanoalkyl malonates are first subjected to the same cyclization reaction as described above. While the resulting cyclic products may be reduced immediately after the formation of ring and then bonded to a synthetic resin, it is preferred that the cyclic products are bonded to the synthetic resin, taking its reactivity into account, prior to the reduction thereof and then reduced.

Synthetic resins which can be used in this invention, are those having functional groups or capable of having introduced therein the functional groups. For example, styrene based synthetic resins, acrylic acid based synthetic resins, polyvinyl alcohol resins and the like can be used. Of these synthetic resins, those containing benzene nuclei in the structure thereof are particularly preferred. These preferred synthetic resins are, for example, polystyrene, a copolymer of styrene and divinyl benzene, etc. They are usually used as ion exchange resins.

Chemical bonding of the above described cyclic reaction products and synthetic resins are achieved by reacting the imino group (=NH) contained in the cyclic reaction products and functional groups such as —Cl, —Br, —I, —COOH, —COOR, —SO$_3$R and the like which are present in the synthetic resins or introduced therein. Of these synthetic resins, polystyrene with chloromethyl groups introduced therein as functional groups is most preferred in effecting the chemical bonding with the cyclic reaction products. Reaction conditions under which the chemical bonding is carried out are not especially limited, and it is sufficient to stir the above cyclic reaction product and the synthetic resin at room temperature or at elevated temperatures. After the above reaction, if necessary, reduction can be carried out.

In this way, synthetic resins to which cyclic tetramines containing a specific substituent are bonded, as represented by Formulas (IV) and (V), can be obtained.

Of the heavy metal ion adsorbents of this invention, cyclic tetramines represented by Formula (II) or (III) have excellent selective adsorption characteristics for heavy metal ions, and furthermore their selectivities among heavy metal ions are excellent. The presence of the specific substituent at the ring carbon atom increases the adsorption speeds of heavy metal ions and makes the adsorption and desorption markedly easy. Those heavy metal ion adsorbents prepared by chemically bonding cyclic tetramines to synthetic resins such as polystyrene and the like, as represented by Formula (IV) or (V) are insoluble in water, and thus they will find a wide variety of applications.

Thus the heavy metal ion adsorbents of this invention can be extensively and effectively used in a wide variety of applications e.g., treatment of waste water, refining of metals, capturing useful metals from sea water, and concentration of metals in the isotope dilution analysis.

We have succeeded in developing various kinds of heavy metal ion adsorbents during the course of conducting various experiments and researches. Among these heavy metal ion adsorbents, those represented by Formula (I) are presently considered to be the most excellent.

Hereinafter, the general explanation of a group of heavy metal ion adsorbents developed by us will be made.

Our heavy metal ion adsorbents are those prepared by chemically bonding large cyclic compounds containing therein at least one nitrogen or sulfur atom as hetero atoms of the ring and having one or more alkyl groups containing three or more carbon atoms of the main chain as substituents at one or more carbon atoms of the ring, said alkyl groups have one or more amino or mercapto groups at one or more carbon atoms of the 3 to 8 positions, to synthetic resins.

The number of atoms forming the ring of the large cyclic compound in the above absorbents is not especially limited in its size, but it is preferred that it is large enough to capture therein heavy metal ions. Thus, the number of atoms forming the ring of the large cyclic compound is desired to be 12 to 18. While the ring number of atoms other than the carbon atoms; i.e., hetero atoms is not especially limited, it is preferably 3 to 6.

These hetero atoms include nitrogen, sulfur and oxygen. It is preferred that the hetero atoms contained in the ring are all nitrogen, or nitrogen and sulfur, or nitrogen and oxygen. In particular, it is most suitable that all of the hetero atoms are nitrogen. In addition, those rings where all of the hetero atoms are sulfur, or sulfur and oxygen, can be considered. These large cyclic compounds include structures in which the hetero atoms are adjacent to each other. In general, however, those structures where 2 to 3 carbon atoms are present between the hetero atoms, are preferred.

The substituents introduced into one or more carbon atoms of the ring (usually one carbon atom) are alkyl groups containing at least 3 carbon atoms, usually 3 to 8 carbon atoms, and preferably 4 to 6 carbon atoms of the main chain, which are substituted by amino or mercapto groups at the 3 to 8 positions of the main chain thereof (preferably in the 4 to 6 positions and most preferably in the ω-position). These alkyl groups are, for example, 4-aminobutyl: —CH$_2$CH$_2$CH$_2$CH$_2$NH$_2$, 4-mercaptobutyl: —CH$_2$CH$_2$CH$_2$CH$_2$SH, and the like. In the large cyclic compounds, the substituents, alkyl groups are introduced at one or more carbon atoms of the ring. Introduction of the substituents at the hetero atoms of the ring are not preferred.

Introduction of alkyl groups containing only 1 to 2 carbon atoms or alkyl groups being substituted by the amino or mercapto group in the α- or β-position of the main chain does not increase the adsorption ability appreciably as compared with those to which no alkyl group is introduced. Thus, no effect can be obtained by the introduction of alkyl groups of 1 or 2 carbon atoms.

In general, the large cyclic compounds can be synthesized in one or two steps by condensation reaction of the compounds containing —NH$_2$, —NHX (X: sulfonyl, acyl, etc.), —OH, —SH or the like at the both ends of the molecular thereof (hereinafter referred to as "Group A Compounds") and the compounds containing —Cl, —Br, —I, —COOH, —COOR or —SO$_3$R (R: alkyl or aryl) at the both ends of the molecular thereof (hereinafter referred to as "Group B Compounds"). It is difficult from the stand point of synthesis to introduce the above described substituents after the ring is formed by the condensation of Group A Compounds and Group B Compounds. Usually, therefore, it is advantageous that Group B Compounds in which the substituents have been introduced, and Group A Compounds are condensed.

Among the condensation reactions of Group A Compounds and Group B Compounds (or Group B Compounds with substituents introduced therein), those condensations of compounds containing —NH$_2$ at the both ends of the molecule of the compound, e.g., ethylenediamine etc. and compounds containing —Br at the both ends of the molecule of the compound, e.g., 1,2-dibromoethane (or those to which the desired substituents have been introduced) yield the objective cyclic compounds in one step. However, those cyclic compounds prepared by reacting ethylenediamine, etc., and diester or dicarboxylic acids (or those to which the desired substituents have been introduced), etc., containing —COOR, —COOH at the both ends of the molecule of the compounds, have insufficient adsorption ability for heavy metal ions as they are. Therefore, it is necessary that these cyclic compounds are reduced to produce large cyclic compounds having sufficient adsorption ability. In the latter case, immediately after the formation of the ring, the cyclic compound obtained may be reduced to provide thereto sufficient adsorption ability and thereafter it may be bonded to a synthetic resin as described hereinafter. Taking the reactivity into account, however, it is preferred that the cyclic compound is bonded to the synthetic resin prior to the reduction thereof and it is then reduced.

With regard to the substituents to be introduced into the large cyclic compounds, introduction of an alkyl group containing a cyano group previously into Group B Compounds or directly into large cyclic compounds is easier than that of an alkyl group containing an amino or mercapto group. Therefore, it is advantageous from the standpoint of synthesis that a large cyclic compound having an alkyl group substituted by an amino group as a substituent is prepared by introducing an alkyl group substituted by a cyano group into a cyclic compound, bonding the resulting cyclic compound to a synthetic resin, and then reducing the cyano group into an amino group along with reduction of the cyclic compound.

For preparing those containing a mercapto group, a method comprising converting the above amino group into a hydroxy group by the use of nitrous acid and the like, and reacting the hydroxy group with phosphorous pentasulfide while heating, and other procedures can be employed. Some of the other procedures are given below:

A substituent containing a carbon-carbon double bond is introduced during the cyclization reaction, and the resulting cyclic compound having the substituent is reacted with thioacetic acid or the like to introduce

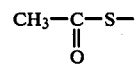

to the carbon-carbon double bond. The resulting cyclic compound is then reduced with borane etc. and bonded to a synthetic resin, or first bonded to a synthetic resin and reduced with borane etc. Thus, the desired product is obtained. In accordance with another procedure, a substituent containing a hydroxy group is introduced during the cyclization reaction, the hydroxy group is replaced by chlorine by the use of sulfonyl chloride or the like, and the chlorine is then converted into a mercapto group by the use of thiourea or the like.

The following are representative examples of combinations of Group A Compounds and Group B Compounds for production of the large cyclic compounds:

1,3-Diaminopropane and 1,3-dibromopropane are reacted in an ethanol solvent in the presence of potassium hydroxide to form 1,5,9,13-tetraazatridecane. This 1,5,9,13-tetraazatridecane is condensed with 3-cyanopropyl malonic diester whereby a cyclic compound having a total number of the ring atoms of 16 containing 4 nitrogen atoms as hetero atoms of the ring can be obtained.

According to another procedure, ethylenediamine ditocylate obtained by reacting tocyl chloride and ethylenediamine is reacted with a compound prepared by introducing a ω-cyanoalkyl group into ethyl bromoacetate. The resulting reaction product is condensed with diethylenetriamine whereby a cyclic compound having a total number of the ring atoms of 15 containing 5 nitrogen atoms as hetero atoms of the ring can be obtained.

According to still another procedure, 1,4,8,11-tetraazaundecane and diethyl 3-cyanopropyl malonate are condensed whereby a cyclic compound having a total number of the ring atoms of 14 containing 4 nitrogen atoms as hetero atoms of the ring can be obtained.

Cyclic compounds containing atoms other than nitrogen as hetero atoms of the ring can be produced by several procedures. For example, ethyleneglycol is converted into disodium ethylenedioxide in methanol by the use of a sodium metal, the disodium ethylenedioxide is reacted with a compound prepared by introducing a ω-cyanoalkyl group to ethyl bromoacetate, and the resulting product is reacted with diethylenetriamine whereby a cyclic compound having a total number of the ring atoms of 15 containing 3 nitrogen and 2 oxygen atoms as hetero atoms of the ring can be obtained.

In accordance with another procedure, a ω-cyanoalkyl group is introduced into 1,6-dimethoxycarbonyl-2,5-dithiahexane and the resulting compound is reacted with diethylenetriamine whereby a cyclic compound having a total number of the ring atoms of 15 containing 3 nitrogen and 2 sulfur atoms as hetero atoms of the ring can be obtained.

The heavy metal ion adsorbents which we have developed are synthesized by bonding the above large cyclic compounds to the synthetic resins as described above, and if necessary, by reducing the resulting products.

The chemical bonding of the large cyclic compounds and the synthetic resins is achieved by reacting functional groups such as —$NH_2$, =NH, —OH, —SH and the like which are originally present in the large cyclic compounds or introduced thereto, and functional groups such as —Cl, —Br, —I, —COOH, —COOR, —$SO_3R$ and the like which are present in the synthetic resins or introduced thereto. It is also possible to replace the functional groups of the large cyclic compounds with those of the synthetic resins. For example, when polyvinyl alcohol (containing —OH as a functional group) is employed as a synthetic resin, the groups —Cl, —Br, —I, —COOH, —COOR, —$SO_3R$ and the like are preferably employed as functional groups of the large cyclic compounds. Of these synthetic resins, polystyrene with a chloromethyl group introduced therein as a functional group is most preferred in chemical bonding with a cyclic compound.

Conditions under which the large cyclic compound and the synthetic resin are chemically bonded will vary depending upon their functional groups. For example, where a large cyclic compound containing an amino or imino group and polystyrene with a chloromethyl group introduced therein are employed, the chemical bonding can be carried out by stirring both at room temperature or elevated temperatures.

After the large cyclic compound and the synthetic resin are chemically bonded, if necessary, the resulting product is reduced, and thus a large cyclic compound with a predetermined substituent introduced therein is obtained which has excellent adsorption ability for heavy metal ions.

These large cyclic compounds bonded to synthetic resins have also excellent selective adsorption abilities for heavy metal ions like the heavy metal ion adsorption of this invention.

The following examples are given to illustrate this invention in more detail.

EXAMPLE 1

(1) Synthesis of Diethyl 3-Cyanopropyl malonate

To a 1-liter three neck flask equipped with a stirrer, a condenser with a drying tube, and a dropping funnel were charged 500 milli liters of anhydrous ethanol and 23 g (1 mole) of a sodium metal. After the sodium metal was completely dissolved, 165 g (1.03 moles) of diethyl malonate was dropped through the dropping funnel at 50° C. Then, 148 g (1 mole) of 3-cyanopropylbromide was dropped. The reaction mixture was refluxed with heating for 3 hours. After the major portion of the solvent was distilled away, 400 milli liters of water were added to the residue and the organic phase was isolated. On distilling the organic phase under reduced pressure, 186 g of diethyl 3-cyanopropyl malonate with a boiling point of 135° C./4 mmHg was obtained (yield 82%). Infrared spectrum showed the peaks: 2250 $cm^{-1}$ and 1740 $cm^{-1}$.

(2) Synthesis of 3-(3-Cyanopropyl)-2,4-dioxo-1,5,8,11-tetraazacyclotridecane

To a 2-liter three neck flask equipped with a cooler and a stirring device were charged 14.6 g (0.1 mole) of triethylenetetramine on the market and a solution prepared by dissolving 22.7 g (0.1 mole) of diethyl 3-cyanopropyl malonate synthesized in (1) in 1 liter of 95% ethanol. The resulting mixture was refluxed with heating and stirring for 5 days. The major portion of ethanol was distilled away from the reaction mixture under reduced pressure. The residues were cooled and crystals precipitated were collected. These crystals were recrystallized from ethanol. Thus, 6.9 g (0.025 mole) of crystals of 3-(3-cyanopropyl)-2,4-dioxo-1,5,8,11-tetraazacyclotridecane (hereinafter referred to as "C-substituted cyclic diamide") was obtained (yield 25%).

The analytical results of the crystals obtained are shown below:

(1) Melting Point: 196°–198° C.

(2) Elemental Analysis: $C_{13}H_{23}O_2N_5$

|   | Found(%) | Calculated(%) |
|---|----------|---------------|
| C | 55.49    | 55.52         |
| H | 8.61     | 8.19          |
| N | 24.56    | 24.91         |

(3) Peaks of Mass Spectrum: m/e: 281 ($M^+$), 238

(4) NMR Spectrum (heavy methanol solvent, TMS base): δ (ppm), 3.48–3.90 (2H, m), 3.28 (1H, t, J=7.0

Hz), 2.95–3.20 (2H, m), 2.73 (8H, m), 2.58 (2H, t, J=7.0 Hz), 1.90 (4H, m).

(3) Synthesis of 3-(4-Amino-n-butyl)-1,5,8,11-tetraazacyclotridecane

To 30 ml of a solution of diborane (18 milli moles) in tetrahydrofuran was added little by little 5 milli moles of the C-substituted cyclic diamide obtained in (2). The mixture was allowed to stand for 30 minutes, and the tetrahydrofuran was distilled away by heating for 5 hours. To the residue was added 20 milli liters of 6 normal hydrochloric acid, and the resulting mixture was heated for 3 hours. Then, the solvent was distilled away under reduced pressure. The residue was further dissolved in a mixed solvent of ethanol-water (5:1) by heating, and then it was cooled. Thus, the hydrochloric acid salt of 3-(4-amino-n-butyl) -1,5,8,11-tetraaza-cyclotridecane precipitated.

A column was charged with about 400 milli liters of an anionic exchange resin (Amberlite IRA-400) which had been washed with an aqueous solution of sodium hydroxide, and water. A solution prepared by dissolving the above hydrochloric acid salt in about 150 milli liters of water was flowed through the column and then about 500 milli liters of water was flowed down through the column. From the effluent so obtained, water was distilled away, and thus 3-(4-amino-n-butyl)-1,5,8,11-tetraaza-cyclotridecane was obtained in high yield.

EXAMPLE 2

(1) Synthesis of Chloromethyl Polystyrene

To a round bottom flask equipped with a stirring device was charged 20 g of polystyrene having a degree of polymerization of 1,600 to 1,800, available on the market, and 124 g (1.54 moles) of chloromethyl methyl ether. The polystyrene was dissolved in the ether by stirring at room temperature. To the solution was added 3.14 g (0.023 mole) of anhydrous zinc chloride powder, and the resulting mixture was stirred at room temperature (20° C.) for 10 hours. The major portion of an excess of chloromethyl methyl ether was distilled away from the reaction mixture at 10° C. under reduced pressure. To the residue was added 150 milli liters of chloroform, and and mixture was filtered to remove the insoluble material. 300 milliliters of methanol were added to the filtrate, and the precipitates were filtered. On drying the precipitates at 60° C. under reduced pressure, 15 g of chloromethyl polystyrene was obtained. The chloromethyl polystyrene was dissolved in heavy chloroform and measured in a degree of chloromethylation. NMR spectrum showed that the degree of chloromethylation per phenyl ring of the starting material, polystyrene, was 60%.

(2) Bonding of C-substituted Cyclic Diamide and Chloromethyl Polystyrene n 30 milli liters of chloroform was dissolved 0.89 g of chloromethyl polystyrene (containing 4 milli moles of chloromethyl group) obtained in (1). To this solution was added 1.124 g (4 milli moles) of 3-(3-cyanopropyl)-2,4-dioxo-1,5,8,11-tetraaza-cyclotridecane obtained in (2) of Example 1, and the resulting mixture was stirred at room temperature for 48 hours. Thus, an insoluble reaction product precipitated. This precipitate was filtered, washed with a 0.1 normal aqueous solution of hydrochloric acid, then washed with distilled water, an aqueous solution of 0.1 normal sodium hydroxide, distilled water, chloroform and methanol in this order, and dried under reduced pressure at 80° C. for 12 hours. As a result, 1.3 g of a white solid compound in which polystyrene was chemically bonded to the C-substituted cyclic diamide, was obtained.

(3) Reduction of C-substituted Cyclic Diamide bonded to Polystyrene 500 mg of the compound obtained in (2) was pulverized to 100–200 meshes, added little by little to 30 milli liters of a solution of diborane (14 milli moles) in tetrahydrofuran while cooling, allowed to stand at room temperature for 30 minutes and then heated at 65° C. for 5 hours. The solvent, tetrahydrofuran was distilled away from the reaction solution. To the residue was added 30 milli liters of a 6 normal aqueous solution of hydrochloric acid, and the resulting mixture was heated at 70° C. for 3 hours. The reaction product was filtered, washed with water, then washed with a 1 nomral aqueous solution of sodium hydroxide, distilled water, chloroform and finally methanol in this order, and dried under reduced pressure at 80° C. for 12 hours. Thus, the objective product; i.e, C-substituted cyclic polyamine: 3-(4-amino-n-butyl) -1,5,8,11-tetraaza-cyclotridecane produced by the reduction of the C-substituted cyclic diamide which was bonded to polystyrene was obtained in the amount of 380 mg. This product was a white solid.

The elemental analysis of the product was as follows: C, 74.91%; H, 9.49%; N, 9.35%.

From these results, it was calculated that C-substituted cyclic polyamine (milli mole)/polystyrene (g)=1.34. Furthermore, it was found that the introduction ratio of C-substituted cyclic polyamine to chloromethylated styrene unit; i.e., conversion was 43%.

(4) Metal Adsorption Test

The compound (containing 0.18 milli mole of C-substituted cyclic polyamine) obtained in (3), in which 3-(4-amino-n-butyl)-1,5,8,11-tetraaza-cyclotridecane was chemically bonded to polystyrene, was pulverized to 100–200 mesh, and added in an amount of 134 mg to each of 3 milli liters of 0.02 mole aqueous solutions of copper, nickel and cobalt sulfates. After the equilibrium at 25° C. was attained, the concentration of remaining metal ion was measured by the atomic absorption. The results obtained are shown in Table 1. In Table 1, the values in the brackets indicate the results obtained by using a compound in which 1,5,8,11-tetraaza-cyclotridecane containing no substituent at the ring carbon thereof was bonded to polystyrene, which is given for comparison.

Table 1

| Metal Ion | Initial Concentration(ppm) | Residual Concentration(ppm) |
|---|---|---|
| $Cu^{2+}$ | 1270 | 1.5 (7) after 24 hours |
| $Ni^{2+}$ | 1174 | 0.25 (7) after 96 hours |
| $Co^{2+}$ | 1180 | 2.5 (22) after 96 hours |

(5) 100 mesh powder of a compound in which 3-(4-amino-n-butyl)-1,5,8,11-tetraaza-cyclotridecane (C-substituted cyclic polyamine) was chemically bonded to polystyrene, was added to each of 3 milli liters of 0.02 mole aqueous solutions of nickel and cobalt sulfates in such an amount that the amount of the C-substituted cyclic compound contained was 0.09 milli mole. In this case, the half-life period of metal ion remaining in the aqueous solution was measured at 25° C. The results are as follows:

| Nickel ion | 30 minutes | (2 hours) |
| Cobalt ion | 30 minutes | (2 hours) |

The values shown in the brackets indicates the results obtained by using a compound as an adsorbent in which 1,5,8,11-tetraaza-cyclotridecane was bonded to polystyrene, which are given for comparison.

EXAMPLE 3

(1) Synthesis of 3-(3-Cyanopropyl)-2,4-dioxo-1,5,8,12-tetraaza-cyclotridecane

The procedure of (2) of Example 1 was repeated with the exception that N,N'-bis(2-aminoethyl)-1,3-propylenediamine was used in place of triethylenetetramine. Thus, 3-(3-cyanopropyl)-2,4-dioxo-1,5,8,12-tetraaza-cyclotetradecane (C-substituted cyclic diamide) was obtained in a yield of 30%.

The analytical results of this C-substituted cyclic diamide are shown below:
(1) Melting Point: 178°–180° C.
(2) Elemental Analysis: $C_{14}H_{25}O_2N_5$

|   | Found(%) | Calculated(%) |
|---|---|---|
| C | 57.00 | 56.92 |
| H | 8.68 | 8.53 |
| N | 23.50 | 23.71 |

(3) Peaks of Mass Spectrum: m/e: 295 (M+)
(4) NMR Spectrum (heavy methanol solvent, TMS base) δ (ppm) 7.50 (2H, broad), 3.60–3.05 (4H, m), 3.20 (1H, t, J=6 Hz), 2.70 (8H, m), 2.41 (2H, s), 2.00 (2H, m), 1.70 (4H, m), 1.41 (2H, t, J=6 Hz)

(2) Synthesis of 3-(4-Amino-n-butyl)-1,5,8,12-tetraaza-cyclotetradecane

The C-substituted cyclic diamide (5 milli moles) obtained in (1) was added little by little while cooling to 30 milli liters of a solution of diborane (18 milli moles) in tetrahydrofuran, allowed to stand for 30 minutes and then heated for 5 hours to distill away the tetrahydrofuran. To the residue was added 20 milli liters of 6 normal hydrochloric acid. The mixture was heated for 3 hours and the solvent was distilled away under reduced pressure. The residue was dissolved in a mixed solvent of ethanol-water (5:1) by heating. On cooling the solution obtained above, the hydrochloric acid salt precipitated.

About 400 milli liters of an anion exchange resin (Amberlite IRA-400) which had been washed with aqueous solution of sodium hydroxide and water was charged to a column. The above hydrochloric acid salt dissolved in about 150 milli liters of water was flowed through the above column, and further about 500 milli liters of water was flowed down through the column. On distilling away the water from the effluent obtained, colorless crystals were obtained in a yield of 70%.

The analytical results of these crystals are shown below:
(1) Melting Point: 132°–133° C.
(2) Elemental Analysis: $C_{14}H_{33}N_5 \cdot H_2O$

|   | Found(%) | Calculated(%) |
|---|---|---|
| C | 59.17 | 58.09 |
| H | 11.93 | 12.19 |
| N | 24.19 | 24.20 |

(3) Peaks of Mass Spectrum: m/e: 271 (M+)
(4) NMR Spectrum (heavy methanol solvent, TMS base) δ (ppm) 2.90–2.50 (5H, m), 1.72 (2H, q), 2.30 (6H, s), 1.36 (6H, s, J=6 Hz)

Analysis of the above date revealed that the crystal was 3-(4-amino-n-butyl)-1,5,8,12-tetraaza-cyclotetradecane.

(3) Metal Adsorption Test

A compound in which 3-(4-amino-n-butyl)-1,5,8,12-tetraaza-cyclotetradecane was chemically bonded to polystyrene, was found in the same manner as in Example 2 except that the C-substituted cyclic diamide obtained in (1) was used. With this compound, the same adsorption test as in (4) of Example 2 was conducted. The results obtained are shown in Table 2. The values in the brackets indicate the results obtained by using a compound in which 1,5,8,12-tetraaza-cyclotetradecane was chemically bonded to polystyrene, which are given for comparison.

Table 2

| Metal Ion | Initial Concentration(ppm) | Residual Concentration(ppm) |   |
|---|---|---|---|
| $Cu^{2+}$ | 1270 | 2.5 | (2.0) |
| $Ni^{2+}$ | 1174 | 18 | (63) |
| $Co^{2+}$ | 1180 | 38 | (134) |

A found value of the elemental analysis of the compound in which 3-(4-amino-n-butyl)-1,5,8,12-tetraaza-cyclotetradecane (C-substituted cyclic polyamine) was chemically bonded to polystyrene, was as follows C, 74.52%; H, 8.72%; N, 9.76%.

From these results, it was calculated that C-substituted cyclic polyamine (m mole)/polystyrene (g)=1.35. Furthermore, it was found that the introduction ratio of C-substituted cyclic polyamine to chloromethylated styrene unit; i.e., converstion was 45%.

(4) 100 mesh powder of a compound in which 3-(4-amino-n-butyl)-1,5,8,12-tetraaza-cyclotetradecane (C-substituted cyclic polyamine) was chemically bonded to polystyrene, was added to each of 3 milli liters of 0.02 mole aqueous solutions of nickel and cobalt sulfates in such an amount that the amount of the C-substituted cyclic compound contained be 0.09 milli mole. In this case, the half-life period of metal ion remaining in the aqueous solution was measured at 25° C. The results are as follows:

| Nickel ion | 1 hour | (6 hours) |
| Cobalt ion | 1 hour | (24 hours) |

The values shown in the brackets indicate the results obtained by using a compound in which 1,5,8,12-tetraaza-cyclotetradecane was chemically bonded to polystyrene, which are given for comparison.

EXAMPLE 4

A compound in which 3-(4-amino-n-butyl)-1,5,9,13-tetraaza-cyclohexadecane was chemically bonded to polystyrene, was synthesized in the same manner as in Examples 1 and 2 except that N,N'-bis(3-aminopropyl)-1,3-propylenediamine was used in place of triethylenetetramine.

The compound obtained is represented by the following formula:

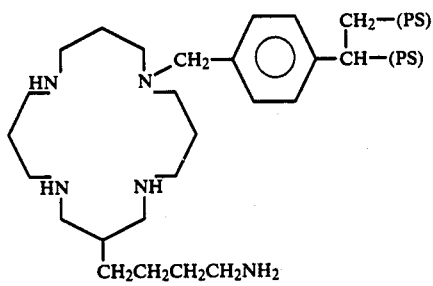

wherein (PS) is polystyrene. With this compound, the same adsorption test as described in (4) of Example 2 was conducted. The results obtained are shown in Table 3. The values shown in the brackets indicate the results obtained by using a compound in which 1,5,9,13-tetraaza-cyclohexadecane was chemically bonded to polystyrene, which are given for comparison.

Table 3

| Metal Ion | Initial Concentration(ppm) | Residual Concentration(ppm) | |
|---|---|---|---|
| $Cu^{2+}$ | 1270 | 3.6 | (8.6) |
| $Ni^{2+}$ | 1174 | 10 | (112) |
| $Co^{2+}$ | 1180 | 19 | (163) |

A found value of the elemental analysis of the compound in which 3-(4-amino-n-butyl)-1,5,9,13-tetraaza-cyclohexadecane (C-substituted cyclic polyamine) was chemically bonded to polystyrene, was as follows: C, 77.23%; H, 8.20%; N, 8.40%. From these results, it was calculated that C-substituted cyclic polyamine (milli mole)/polystyrene (g) = 1.20. Further, it was found that the introduction ratio of C-substituted cyclic polyamine to chloromethylated styrene unit; i.e., conversion was 37%.

What is claimed is:

1. A heavy metal ion absorbent represented by the formula:

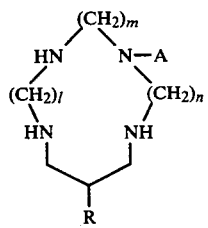

wherein l, m and n are 2 or 3, respectively; R is an alkyl group containing 4 to 6 carbon atoms which is substituted by an amino group in the ω-position; and A is hydrogen or polystyrene.

2. The heavy metal ion adsorbent according to claim 1, which is represented by the formula:

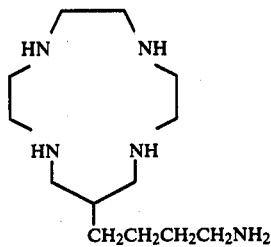

3. The heavy metal ion adsorbent according to claim 1, which is represented by the formula:

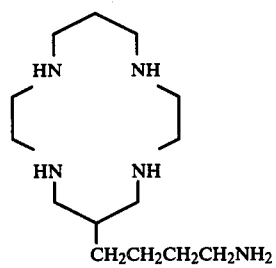

4. The heavy metal ion adsorbent according to claim 1, which is represented by the formula:

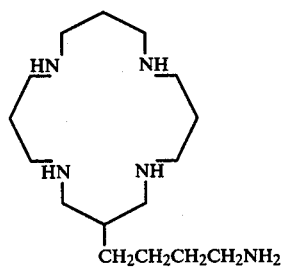

5. The heavy metal ion adsorbent according to claim 1, which is represented by the formula:

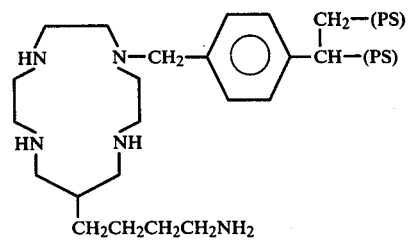

wherein (PS) is polystyrene.

6. The heavy metal ion adsorbent according to claim 1, which is represented by the formula:

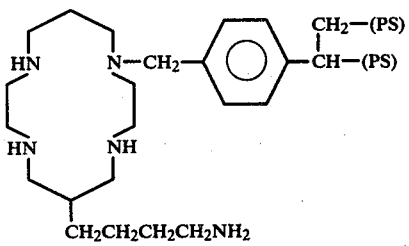

wherein (PS) is polystyrene.

7. The heavy metal ion adsorbent according to claim 1, which is represented by the formula:

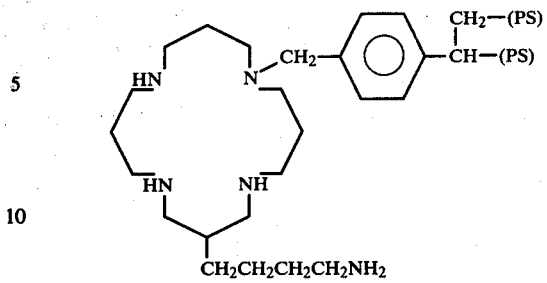

wherein (PS) is polystyrene.

8. The heavy metal ion adsorbent according to claim 1, wherein A is hydrogen.

9. The heavy metal ion adsorbent according to claim 1, wherein A is polystyrene.

10. The heavy metal ion adsorbent according to claim 1, wherein l equals n.

11. The heavy metal ion adsorbent according to claim 1, wherein the nitrogen and carbon containing ring contains a total of 13 ring atoms.

12. The heavy metal ion adsorbent according to claim 1, wherein the nitrogen and carbon containing ring contains a total of 14 ring atoms.

13. The heavy metal ion adsorbent according to claim 1, wherein the nitrogen and carbon containing ring contains a total of 15 ring atoms.

14. The heavy metal ion adsorbent according to claim 1, wherein the nitrogen and carbon containing ring contains a total of 16 ring atoms.

* * * * *